United States Patent [19]
Adkins et al.

[11] Patent Number: 6,004,482
[45] Date of Patent: *Dec. 21, 1999

[54] STABLE AROMATIC AMINE COMPOSITION, AND A PROCESS FOR PREPARING COLOR STABLE AROMATIC AMINES

[75] Inventors: Rick L. Adkins, New Martinsville, W. Va.; Steven L. Schilling, Pittsburgh, Pa.; Keith J. Headley, Paden City, W. Va.

[73] Assignee: Bayer Corporation, Pittsburgh, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/998,141

[22] Filed: Dec. 24, 1997

[51] Int. Cl.$^6$ .................................................. C09K 15/32
[52] U.S. Cl. ...................... 252/400.62; 252/401; 564/437
[58] Field of Search ...................... 564/437; 252/400.62, 252/401

[56] References Cited

U.S. PATENT DOCUMENTS

| | | | |
|---|---|---|---|
| 3,264,268 | 8/1966 | Muller et al. | 260/77.5 |
| 3,314,995 | 4/1967 | Cross et al. | 260/570 |
| 3,446,848 | 5/1969 | Aitken et al. | 260/584 |
| 3,462,492 | 8/1969 | Kober | 260/573 |
| 3,499,009 | 3/1970 | Odinak et al. | 260/570 |
| 3,674,787 | 7/1972 | Frey et al. | 260/247.2 A |
| 3,914,418 | 10/1975 | Patchett et al. | 424/230 |
| 4,172,833 | 10/1979 | Whitney et al. | 548/105 |
| 4,209,609 | 6/1980 | Haas | 528/421 |
| 4,391,728 | 7/1983 | Korczak et al. | 252/182 |
| 4,421,871 | 12/1983 | Korczak et al. | 521/167 |
| 4,562,290 | 12/1985 | Korczak et al. | 564/399 |
| 4,868,283 | 9/1989 | Bartmann et al. | 528/480 |
| 4,877,879 | 10/1989 | Gansow | 544/402 |
| 4,885,371 | 12/1989 | Tracy et al. | 548/554 |
| 5,113,017 | 5/1992 | Smith et al. | 564/2 |
| 5,196,585 | 3/1993 | Wirth | 564/437 |
| 5,449,832 | 9/1995 | Van Court Carr et al. | 564/422 |
| 5,693,862 | 12/1997 | Keyvani et al. | 564/305 |

FOREIGN PATENT DOCUMENTS

| | | |
|---|---|---|
| 0 581 100 | 2/1994 | European Pat. Off. . |
| 1073664 | 6/1967 | United Kingdom . |
| 1311095 | 3/1973 | United Kingdom . |
| 1398185 | 6/1975 | United Kingdom . |

OTHER PUBLICATIONS

Database WPI Sec. Ch., AN 93–365377, XP002097674 & JP 05 271481 A (Sumitomo Chem Co Ltd) Oct. 19, 1993.

*Primary Examiner*—Samuel Barts
*Attorney, Agent, or Firm*—Joseph C. Gil; N. Denise Brown

[57] ABSTRACT

This invention relates to stable aromatic amine compositions. These compositions comprise a) a compound selected from the group consisting of alkali metal salts of sulfur compounds, hydrates thereof and aldehydes thereof, aluminum hydrides, borates and boron compounds; and b) an aromatic amine. This invention also relates to a process for stabilizing the color of aromatic amines, and to the production of polyether polyols from these stable aromatic amine compositions.

18 Claims, No Drawings

STABLE AROMATIC AMINE COMPOSITION, AND A PROCESS FOR PREPARING COLOR STABLE AROMATIC AMINES

BACKGROUND OF THE INVENTION

This invention relates to a composition comprising an aromatic amine compound and a small quantity of a stabilizing compound. The present invention also relates to a method for preventing the discoloration of aromatic amines, and to a process for the production of light colored aromatic amine based polyether polyols.

One of the problems or disadvantages associated with amine group containing compounds is the tendency of these compounds to discolor. Some amine group containing compounds such as, for example, ortho-toluenediamine (o-TDA), darken almost immediately upon exposure to air, while others such as, for example, aniline, are more stable and darken more slowly over time. The aliphatic amine group containing compounds also discolor over time at room temperature, but generally speaking, these discolor at a much slower rate than the aromatic amine group containing compounds.

Amine group containing compounds are known to be suitable initiators for preparing polyether polyols. Various amine initiated polyether polyols and the process for their production are described in, for example, U.S. Pat. Nos. 3,264,268, 3,314,995, 3,446,848, 3,462,492, 3,499,009, 4,209,609, 4,391,728, 4,421,871 and 4,562,290, and in British Patents 1,073,664, 1,311,095 and 1,398,185.

The use of discolored amine group containing compounds as initiators in the production of polyether polyols results in the polyether polyols also being discolored. Although it may be possible to reduce the dark color of the resultant polyether polyols, it is preferred that discoloration of these polyether polyols be prevented. Accordingly, a means of preventing discoloration of amine group containing compounds and/or reducing the color of polyether polyols started from amine group containing compounds is commercially desirable.

One way of avoiding/preventing discoloration of these amine group containing compounds and polyether polyols prepared from these compounds, is to immediately form polyether polyols from the amine group containing compounds after purification (usually distillation), before they come into contact with air. This, however, requires that the amine group containing compounds and the resultant polyether polyols be produced in the same plant or nearby plants, with little to no time lapse between the point at which the amine containing compounds are distilled and when these are used as initiators to form polyether polyols. Otherwise, stringent engineering measures are required to ensure that the amine compounds are oxygen-free at all points in the process between the time they are purified and used. Currently, it is necessary to keep the entire process after amine purification totally under positive nitrogen or another inert gas pressure to prevent and/or minimize this discoloration.

A process for the preparation of 2-mercaptotoluimidazole and metal salts thereof is described in U.S. Pat. No. 4,172,833. This process comprises reacting a stabilized raw material system comprising o-toluenediamine, a stabilizer, and carbon disulfide in the presence of a solvent, collecting the formed 2-mercaptotoluimidazole by filtration and recovering the solvent for recycling. Suitable stabilizers include hydrazine, hydrazine hydrate and hydrazine salts of strong acids. The addition of these stabilizers to o-toluenediamine prevents color degradation.

U.S. Pat. No. 4,877,879 relates to a process for stabilizing polyether compositions which are prepared from one or more alkylene oxides using an amine initiator. This process comprises contacting the crude polyether composition with a reducing agent in a sufficient quantity to effect the stabilization during or after neutralization. Formic acid and lithium borohydride are two reducing agents disclosed as being suitable. This process requires the addition of an excess amount of formic acid (or another reducing agent) at the end of the polyether reaction to neutralize the alkaline polymerizate. Although aromatic and aliphatic amines are disclosed as being suitable, it is further disclosed that this process is particularly useful when one or more tertiary amines are present in the initiator compound. N-aminoethylpiperazine, an aliphatic amine, is the preferred amine, and is used in all the working examples.

In accordance with the present invention, it was found that the addition of the presently claimed stabilizing compounds to an aromatic amine compound surprisingly formed compositions which are stable against discoloration. This is true even after storing the treated aromatic amine compositions in a 100° C. oven for 4 weeks. Polyether polyols can then be produced from these treated aromatic amine compounds, without the derogatory color effects one would normally expect from an untreated aromatic amine compound.

SUMMARY OF THE INVENTION

This invention relates to stable aromatic amine compositions comprising:

a) from 0.01 to 5% (preferably 0.05 to 1.0%, most preferably from 0.1 to 0.5%) by weight, based on 100% by weight of component b), of a compound selected from the group consisting of alkali metal salts of sulfur compounds, hydrates thereof, and aldehydes thereof; aluminum hydrides; borates; and boron compounds; and b) at least one aromatic amine group containing compound.

The present invention also relates to a process for stabilizing the color of an aromatic amine group containing compound. This process comprises 1) adding a) from 0.01 to 5% (preferably 0.05 to 1.0%, most preferably from 0.1 to 0.5%) by weight, based on 100% by weight of component b), of at least one compound selected from the group consisting of alkali metal salts of sulfur compounds, hydrates thereof, and aldehydes thereof; aluminum hydrides; borates; and boron compounds; to b) at least one aromatic amine group containing compound. Crude toluenediamine and ortho-toluenediamine are preferred aromatic amines in which discoloration can be prevented or minimized by adding a small quantity of one of these compounds.

The present invention also relates to a process for the production of stable, light colored aromatic amine-based polyether polyols comprising alkoxylating an aromatic amine group containing compound, wherein said aromatic amine group containing compound has been treated with from 0.01 to 5% by weight (preferably 0.05 to 1.0%, most preferably 0.1 to 0.5% by weight), based on 100% by weight of the aromatic amine group containing compound, with at least one compound selected from the group consisting of alkali metal salts of sulfur compounds, hydrates thereof, and aldehydes thereof; aluminum hydrides; borates; and boron compounds.

The addition of a small quantity of a stabilizing compound as described above is effective in preventing or minimizing the discoloration of aromatic amine group containing compounds, and thereby allows light colored polyether polyols to be produced therefrom.

DETAILED DESCRIPTION OF THE INVENTION

As used in the present invention, the term stable with respect to the aromatic amine compositions of the present invention means that the Gardner color of these is lighter than the standard when stored for at least 4 weeks at a temperature of ≧25° C. The standard is the corresponding untreated aromatic amine.

In accordance with the present invention, suitable compounds for treating aromatic amines to prevent discoloration are compounds including alkali metal salts of sulfur compounds, hydrates thereof, and aldehydes thereof; aluminum hydrides; borates; and boron compounds.

Suitable compounds to be used as alkali metal salts of sulfur compounds, the hydrates thereof and/or aldehydes thereof include, for example, sodium hydrosulfite, lithium hydrosulfite, potassium hydrosulfite, sodium hydrosulfide hydrate, lithium hydrosulfide hydrate, potassium hydrosulfide hydrate, formaldehyde sodium bisulfite, formaldehyde lithium bisulfite, potassium lithium bisulfite, acetaldehyde sodium bisulfite, acetaldehyde potassium bisulfite, acetaldehyde lithium bisulfite, etc. Preferred sulfur compounds are sodium hydrosulfite, sodium hydrosulfide hydrate, formaldehyde sodium bisulfite, and acetaldehyde sodium bisulfite.

Suitable aluminum hydrides include, for example, alkali metal aluminum hydrides such as, for example, lithium aluminum hydride, sodium aluminum hydride, potassium aluminum hydride; dialkyl aluminum hydrides such as, for example, dimethyl aluminum hydride, diethyl aluminum hydride, dipropyl aluminum hydride, diisopropyl aluminum hydride, diisobutyl aluminum hydride, etc.

Suitable compounds for use in the present invention also include borates, hydrides thereof and cyanides thereof. Some examples of such compounds include borates such as, for example, sodium borate, potassium borate, etc.; hydrides of borates such as, for example, sodium borohydride, potassium borohydride, lithium borohydride etc.; and cyanides of borohydrides including alkali metal cyanoborohydrides such as, for example, sodium cyanoborohydride, potassium cyanoborohydride, lithium cyanoborohydride, etc. A preferred borate for the present invention is sodium cyanoborohydride. Lithium boiohydride is of lesser interest in the present invention, and is preferably not used as component a).

Suitable boron compounds for the present invention include compounds such as, for example, hydrides, ammoniates, N-alkylamines, etherates, halide etherates, alkyl sulfides, halide sulfides, polycycloalkanes, etc. Some suitable boron compounds include boron hydrides such as, for example, diborane, borane, etc.; boron ammoniates such as, for example, borane-ammonia complex, etc.; N-alkylamine complexes with borane such as, for example, methylamine borane complex, dimethylamine borane complex, diethylamine borane complex, dipropylamine borane complex, dibutylamine borane complex, etc.; etherates of boron compounds such as, for example, complexes of borane with tetrahydrofuran, diethylether complexes with borane, etc.; halide etherates of boron such as, for example, tioron trifluoride etherate, etc; alkyl sulfide complexes with borane such as, for example, borane-methylsulfide complex, etc.; halide sulfide complexes with boron such as, for example, dibromoborane-methylsulfide complex, dibromoborane-ethylsulfide complex, dilfluoroborane-methylsulfide, dichloroborane-methylsulfide, etc.; and polycycloalkanes containing boron atoms such as, for example, 9-borabicyclo[3.3.1]nonane (9-BBN), 9-BBN dimer, etc.

Preferred boron compounds for the present invention include dimethylamine borane, sodium borohydride, borane-tetrahydrofuran complex, and 9-BBN.

The most preferred compounds for the present invention are sodium borohydride and borane-dimethylamine complex.

Suitable borane containing compounds for use in the present invention can be synthesized by techniques well known to one of ordinary skill in the art. Some examples of suitable synthesis techniques can be found in *Advanced Organic Chemistry*, Jerry March, 2nd Edition, 1977, pp. 718–722, the disclosure of which is herein incorporated by reference. Synthesis techniques for aluminum and sulfur compounds are also well known to the skilled artisan. Some examples of such techniques can be found in, for example, Fieser and Fieser *Reagents For Organic Synthesis*, Vol. 1, 1967, pp. 582 and 1090.

In general, suitable aromatic amine group containing compounds of the present invention have molecular weights of less than about 500 and preferably greater than about 90. It is preferred that the molecular weight of the aromatic amine group containing compounds is less than about 400, and more preferably less than about 200. Suitable aromatic amine group containing compounds include, for example, those compounds wherein at least 1 amine group is, preferably 1 to 3 amine groups, and most preferably 2 amine groups are attached directly to an aromatic ring, and the aromatic ring may be substituted or unsubstituted. Suitable substituents for the aromatic ring include, for example, alkyl groups having from 1 to 18 carbon atoms which may be branched or linear such as, for example, methyl, ethyl, propyl, etc.; aromatic groups having from 6 to 13 carbon atoms such as, for example, phenyl, aminophenyl, and diaminophenyl; and arylalkyl groups having from 7 to 12 carbon atoms such as, for example, methylene(aminophenyl), 2-(aminophenyl)butyl, etc. Suitable substituents for the aromatic ring also include hydroxyl groups. 4-Aminophenol is one example of a compound wherein the aromatic ring is substituted with an hydroxyl group. Also, suitable as the aromatic amine group containing compound of the present invention are fused ring systems containing from 10 to 20 carbon atoms. Diaminonaphthalene is one example of a suitable fused ring system for the present invention.

Examples of suitable aromatic amines for the present invention include compounds such as aniline, diaminobenzene, triaminobenzene, tetraaminobenzene, tetraaminobiphenyl, methylene dianiline, crude toluenediamine (a mixture of the various isomers, i.e. 2,3-TDA, 2,4-TDA, 3,4-TDA, 2,5-TDA, and 2,6-TDA), and ortho-toluenediamine (i.e., an isomeric mixture of primarily 2,3-TDA and 3,4-TDA in a weight ratio of about 60 to about 40). Ortho-toluenediamine and crude toluenediamine are preferred aromatic amines in the present invention.

The preparation of suitable amines for the present invention is well known to those skilled in the art. For instance, suitable amines can be prepared by dinitrating toluene with nitric acid in the presence of sulfuric acid or other catalyst to yield isomers of dinitrotoluene, which are then reduced with hydrogen to yield crude toluenediamine. (See, for example, *Kirk-Othmer Encyclopedia of Chemical Technology*, Fourth Edition, "Amines by Reduction", Volume 2, pp. 483–501, and "Nitrobenzene and Nitrotoluenes", Volume 17, pp. 133–151.) Ortho-toluenediamine can be obtained from crude toluenediamine by distillation.

In the process of the present invention, discoloration of aromatic amines is prevented or minimized by adding a small quantity of at least one stabilizing compound as described above to aromatic amines as soon as possible after the formation and subsequent purification of these amines. The time after an amine is prepared and the point in time at which the addition of a small quantity of one of these compounds is necessary to be effective in preventing discoloration of the amine ultimately depends on the stability of the particular amine with respect to discoloration and how well it is protected from contact with air.

Some relatively stable amines such as, for example, aniline, darken slowly over time while other amines are relatively unstable and darken quickly upon exposure to air. Ortho-toluerediamine is one example of a relatively unstable amine which darkens quickly when exposed to air. Accordingly, the point at which the stabilizing compound is added to the amine to prevent discoloration may vary. It is, however, preferred that a small quantity of a stabilizing compound is added to the amine immediately following distillation. The stabilizing compounds may be added at a later point, if the freshly prepared amine is kept oxygen-free under an inert gas, such as, for example, nitrogen or argon. Once the stabilizing compound(s) has been added to the aromatic amine compound, the resultant composition is relatively stable in terms of color changes.

Typically, in a conventional process, when the nitrogen system fails or a leak occurs in the system protecting the amine group containing compound from exposure to air, the amine group containing compound begins to darken. Ortho-toluenediamine and crude TDA, the preferred amine group containing compounds, start to darken almost immediately upon exposure to air. The presence of a stabilizing agent such as, for example, sodium borohydride, helps protect the color of the amine compound until the nitrogen can be restored.

It is, of course, possible to form a polyether polyol using the previously described aromatic amine compositions. In this embodiment of the present, an aromatic amine which has been treated with a small quantity of a stabilizing compound as described above, is used as the initiator for the polyether polyol instead of a conventional untreated aromatic amine. A polyether polyol prepared from the color stable aromatic amine has a lighter color than a polyether polyol prepared from an untreated aromatic amine. Polyether polyols based on these treated aromatic amine initiators in accordance with the present invention can be prepared by any of the known processes such as are described in, for example, U.S. Pat. Nos. 4,209,609 and 4,421,871, the disclosures of which are herein incorporated by reference, and as described in British Patent 1,398,185. In general, the amine-initiated polyether polyols of the present invention are prepared by reacting an alkylene oxide with an amine having an amine functionality of at least 1, optionally in the presence of an alkaline catalyst.

The suitable amine initiators for preparing polyether polyols include those previously described which have been treated with a compound selected from the group consisting of alkali metal salts of sulfur compounds, hydrates thereof and aldehydes thereof, aluminum hydrides, borates and boron compounds. Some examples of alkylene oxides useful in producing the polyether polyols of the present invention include: ethylene oxide, propylene oxide, butylene oxide, and mixtures of these alkylene oxides. Combinations of ethylene oxide and propylene oxide are particularly preferred. Any suitable catalyst which is capable of catalyzing the epoxidation reaction of the present invention may be used. Some examples of suitable catalysts include alkaline catalysts, double metal cyanides, N-methyimidazoles, boron trifluoride, etc. Specific alkaline catalysts which have been found to be particularly suitable include, for example, potassium hydroxide and sodium hydroxide.

In general, the epoxidation reaction occurs by contacting the amine having an amine functionality of at least 1 with the alkylene oxide(s) at an elevated temperature in the range of from 90 to 180° C. under moderately elevated pressure, optionally in the presence of the alkaline catalyst. The amounts of amine and alkylene oxide which are used are generally 1 to 10 equivalents of alkylene oxide for each equivalent of amine. The epoxidation product generally has an average hydroxyl value (determined by ASTM D-2849-69 hydroxyl number method C) of at least 28, preferably in the range of from about 250 to about 1200. The molecular weights of the polyether polyols of the present invention (number average determined by end group analysis and nominal functionality of the polyol) generally range from about 150 to about 1500, preferably from about 300 to about 1200, most preferably from about 400 to about 1000.

After the polyol has been prepared, the resultant reaction mixture which contains the alkaline catalyst in amounts of from about 0.1% to about 1.0% as KOH is neutralized with an acid such as, for example, sulfuric acid, phosphoric acid, lactic acid or oxalic acid. Neutralization may be accomplished by mixing the acid and reaction mixture at ambient conditions with stirring, then distilling to remove any excess water. The neutralized polyether polyol need not have a pH of exactly 7.0. The reaction mixture may be maintained at a slight acidity or alkalinity, i.e., at a pH of from 5 to 11, preferably from 6 to 10. If the salt formed is soluble in the polyol, it may be left in. Otherwise, the salt can be removed by, for example, filtration.

The neutralized polyether polyol reaction mixture of the present invention is clear, i.e., free from haze and may be used directly in processes for the production of polyurethane foams. Methods for the production of polyurethane foams by reacting these polyether polyols with polyisocyanates via the polyisocyanate addition process are well known to those skilled in the art.

The following examples further illustrate details for the preparation and use of the compositions and processes of this invention. The invention, which is set forth in the foregoing disclosure, is not to be limited either in spirit or scope by these examples. Those skilled in the art will readily understand that known variations of the conditions and processes of the following preparative procedures can be used to prepare these compositions. Unless otherwise noted, all temperatures are degrees Celsius and all parts and percentages are parts by weight and percentages by weight, respectively.

EXAMPLES

Example 1

100 g. of freshly distilled ortho-toluenediamine (o-TDA) were placed in a flask. To this, 0.5 g. of dimethylaminoborane was added, followed by mixing thoroughly. The sample was sealed, and placed in a 65° C. oven, along with a sealed sample of 100 g. of untreated, freshly distilled ortho-toluenediamine (see Example 1 in Table 1). After 24 hours, the untreated sample had a Gardner color >18, but the treated sample had a Gardner color of 5. After 48 hours, the untreated sample of o-TDA was opaque black (i.e., the Gardner color was >>18), whereas the sample treated with dimethylamineborane still had a Gardner color of 5. The color of the o-TDA sample treated with dimethylamineborane was checked at 24 hours, 48 hours, 2 weeks, 4 weeks and 6 weeks, after storage in a 65° C. oven. After 6 weeks, the color of the o-TDA treated with dimethylamineborane was still a Gardner 5.

Examples 2–7

These examples were performed using an essentially identical procedure as set forth under Example 1, with the exception of the particular stabilizing compound which was added to the freshly distilled o-TDA and the amount of each stabilizing compound. Specific stabilizing compounds and the relative quantity of each, as well as the result on the Gardner color after storage in a 65° C. oven for 24 hours, 48 hours, 4 weeks, 6 weeks and 8 weeks are shown in Table 1 below. Since the color of the treated o-TDA samples remained the same throughout storage, the Gardner color is only reported in the table for the longest storage time.

The polyol was heated at 110° C. and 5 mm Hg to reduce the water content and the material was filtered to remove the potassium sulfate salt which was generated. The resultant polyol was characterized by a color of 14 on the Gardner scale.

Polyether Polyol B

A polyether polyol was prepared from untreated o-TDA, in accordance with the following procedure. This untreated molten o-TDA was exposed to air by pouring the molten material back and forth between two open containers several times. 2773 g. of this material was charged to a stirred reactor which was sealed, purged with nitrogen, and pressurized to 30 psig with nitrogen. The material was heated to 115° C., and 3456 g. of ethylene oxide were slowly added to the reactor over 2 hours, then allowed to react for an additional 2 hours. The mixture was cooled to 90° C. and 52.6 g. of a 46% aqueous potassium hydroxide solution was added. After sealing and pressurizing the reactor, it was again heated to 115° C., followed by slowly adding 5881 g. of propylene oxide over 4 hours, and then allowed to react for an additional 3 hours. After cooling to 90° C., 1200 g. of water were added and the KOH was neutralized with an equivalent of sulfuric acid. The polyol was heated at 110° C.

TABLE 1

EFFECT OF TREATMENT OF O-TDA WITH ADDITIVES ON GARDNER COLOR

| Example | Additive | Weight (grams) | Oven Temp. (° C.) | Time (weeks) at Temperature | Gardner Color |
|---------|----------|----------------|-------------------|------------------------------|---------------|
| 1 | dimethylamineborane | 0.5 | 65 | 6 | 5 |
| 2 | sodium borohydride (solid) | 0.5 | 65 | 6 | 5 |
| 3 | sodium borohydride (solid) | 0.5 | 65 | 4 | 13 |
| 4 | sodium borohydride (solid) | 0.5 | 100* | 2 | 13 |
| 5 | sodium borohydride (13% in $H_2O$) | 0.8 | 65 | 8 | 8 |
| 6 | sodium borohydride (13% in $H_2O$) | 1.9 | 65 | 8 | 5 |
| 7 | sodium borohydride (13% in $H_2O$) | 3.8 | 65 | 8 | 8 |
| 8 | untreated | — | 65 | 8 | >18 (opaque black) |

Example 4 is Example 3 placed in a 100° C. oven for 2 weeks, after being placed in a 65° C. oven for 4 weeks.

Example 9

Polyether polyols were prepared from treated o-TDA and untreated o-TDA.

Polyether Polyol A

A polyether polyol was prepared from a treated o-TDA similar to that described in Example 1 above, in accordance with the following procedure. This treated molten o-TDA was exposed to air by pouring the molten material back and forth between two open containers several times. 2680 g. of this material was charged to a stirred reactor which was sealed, purged with nitrogen, and pressurized to 30 psig with nitrogen. The material was heated to 115° C., and 3339 g. of ethylene oxide were added to the reactor over 2 hours, then allowed to react for an additional 2 hours. The mixture was cooled to 90° C. and 50.9 g. of a 46% aqueous potassium hydroxide solution was added. After sealing and pressurizing the reactor with nitrogen, it was again heated to 115° C., followed by slowly adding 5683 g. of propylene oxide over 4 hours, and then allowed to react for an additional 3 hours. After cooling to 90° C., 1200 g. of water were added and the KOH was neutralized with an equivalent of sulfuric acid.

and 5 mm Hg to reduce the water content and the material was filtered to remove the potassium sulfate salt which was generated. The resultant polyol was characterized by a color of >18 (based on the Gardner scale).

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A stable aromatic amine composition comprising:
    a) from 0.01 to 5% by weight, based on 100% by weight of component b), of a compound selected from the group consisting of i) alkali metal salts of sulfur compounds, ii) hydrates of alkali metal salts of sulfur compounds, iii) aldehydes of alkali metal salts of sulfur compounds, iv) aluminum hydrides, and
    b) an aromatic amine group containing compound having at least two amine groups directly attached to the aromatic ring.

2. The composition of claim 1, wherein b) said aromatic amine group containing compound has a molecular weight of less than about 500 and contains from two to three amine groups attached to the aromatic ring, and the aromatic ring is unsubstituted or substituted, with any substituents being selected from the group consisting of:

i) hydroxyl groups,
  ii) alkyl groups having from 1 to 18 carbon atoms which may be branched or linear,
  iii) aromatic groups having from 6 to 13 carbon atoms, and
  iv) arylalkyl groups having from 7 to 12 carbon atoms.

3. The composition of claim 1, wherein b) said aromatic amine group containing compound has a molecular weight of less than about 500 and comprises a fused ring system containing from 10 to 20 carbon atoms, wherein from two to four amine groups are attached to the ring system.

4. The composition of claim 2, wherein b) said aromatic amine group containing compound comprises crude toluenediamine or ortho-toluenediamine.

5. A stable aromatic amine composition comprising:

a) from 0.01 to 5% by weight, based on 100% by weight of component b), of a compound selected from the group consisting of borates and boron compounds; and an aromatic amine group containing compound selected from the group comprising crude toluenediamine or ortho-toluenediamine.

6. The composition of claim 5, wherein a) is selected from the group consisting of borane-dimethylamine and sodium borohydride.

7. A process for stabilizing the color of an aromatic amine comprising:

1) adding from 0.01 to 5% by weight, based on 100% by weight of b), of a) a stabilizing compound to b) an aromatic amine group containing compound having at least two amine groups attached directly to the aromatic ring, wherein said stabilizing compound a) is selected from the group consisting of i) alkali metal salts of sulfur compounds, ii) hydrates of alkali metal salts of sulfur compounds, iii) aldehydes of alkali metal salts of sulfur compounds and iv) aluminum hydrides.

8. The process of claim 7, wherein b) said aromatic amine group containing compound has a molecular weight of less than about 500 and contains from two to three amine groups attached to the aromatic ring, and the aromatic ring is unsubstituted or substituted, with any substituents being selected from the group consisting of:

i) hydroxyl groups,
  ii) alkyl groups having from 1 to 18 carbon atoms which may be branched or linear,
  iii) aromatic groups having from 6 to 13 carbon atoms, and
  iv) arylalkyl groups having from 7 to 12 carbon atoms.

9. The process of claim 6, wherein b) said aromatic amine group containing compound has a molecular weight of less than about 500 and comprises a fused ring system containing from 10 to 20 carbon atoms, wherein from two to four amine groups are attached to the ring system.

10. The process of claim 8, wherein b) said aromatic amine group containing compound comprises crude toluenediamine or ortho-toluenediamine.

11. A process for stabilizing the color of an aromatic amine, comprising:

1) adding from 0.01 to 5% by weight, based on 100% by weight of b), of a) a stabilizing compound selected from the group consisting of borates and boron compounds, to b) an aromatic amine comprising crude toluenediamine or ortho-toluenedianiine.

12. The process of claim 11, wherein a) is selected from the group consisting of borane-dimethylamine and sodium borohydride.

13. A process for the production of a polyether polyol comprising alkoxylating an aromatic amine group containing compound having at least two amine groups attached directly to the aromatic ring, wherein said aromatic amine group containing compound having at least two amine groups attached directly to the aromatic ring is treated with from 0.01 to 5% by weight, based on 100% by weight of aromatic amine, with a compound selected from the group consisting of i) alkali metal salts of sulfur compounds, ii) hydrates of alkali metal salts of sulfur compounds, iii) aldehydes of alkali metal salts of sulfur compounds and iv) aluminum hydrides.

14. The process of claim 13, wherein b) said aromatic amine group containing compound has a molecular weight of less than about 500 and contains from two to three amine groups attached to the aromatic ring, and the aromatic ring is unsubstituted or substituted, with any substituents being selected from the group consisting of:

i) hydroxyl groups,
  ii) alkyl groups having from 1 to 18 carbon atoms which may be branched or linear,
  iii) aromatic groups having from 6 to 13 carbon atoms, and
  iv) arylalkyl groups having from 7 to 12 carbon atoms.

15. The process of claim 13, wherein b) said aromatic amine group containing compound has a molecular weight of less than about 500 and comprises a fused ring system containing from 10 to 20 carbon atoms, wherein from two to four amine groups are attached to the ring system.

16. The process of claim 14, wherein b) said aromatic amine group containing compound comprises crude toluenediamine or ortho-toluenediamine.

17. A process for the production of a polyether polyol comprising alkoxylating an aromatic amine, wherein said aromatic amine comprises crude toluenediamine or ortho-toluenediamine, and is treated with from 0.01 to 5% by weight, based on 100% by weight of aromatic amine, of a compound selected from the group consisting of borates and boron compounds.

18. The process of claim 17, wherein a) is selected from the group consisting of borane-dimethylamine and sodium borohydride.

* * * * *